(12) United States Patent
Brannan et al.

(10) Patent No.: US 10,675,089 B2
(45) Date of Patent: Jun. 9, 2020

(54) MANAGEMENT OF VOLTAGE STANDING WAVE RATIO AT SKIN SURFACE DURING MICROWAVE ABLATION

(71) Applicant: COVIDIEN LP, Mansfield, MA (US)

(72) Inventors: Joseph D. Brannan, Erie, CO (US); Kaylen J. Haley, Westminster, CO (US); Kenlyn S. Bonn, Lakewood, CO (US)

(73) Assignee: COVIDIEN LP, Mansfield, MA (US)

( * ) Notice: Subject to any disclaimer, the term of this patent is extended or adjusted under 35 U.S.C. 154(b) by 427 days.

(21) Appl. No.: 14/804,656

(22) Filed: Jul. 21, 2015

(65) Prior Publication Data

US 2015/0320495 A1   Nov. 12, 2015

Related U.S. Application Data

(63) Continuation of application No. 12/568,883, filed on Sep. 29, 2009, now Pat. No. 9,113,926.

(51) Int. Cl.
*A61B 18/18* (2006.01)
*A61B 18/00* (2006.01)

(52) U.S. Cl.
CPC .......... *A61B 18/18* (2013.01); *A61B 18/1815* (2013.01); *A61B 2018/00023* (2013.01); *A61B 2018/00577* (2013.01); *A61B 2018/00714* (2013.01); *A61B 2018/00744* (2013.01); *A61B 2018/00791* (2013.01); *A61B 2018/1869* (2013.01); *A61B 2018/1892* (2013.01)

(58) Field of Classification Search
CPC ................ A61B 18/18; A61B 18/1815; A61B 2018/00023; A61B 2018/00577; A61B 2018/00714; A61B 2018/00744; A61B 2018/00791; A61B 2018/1869; A61B 2018/1892
See application file for complete search history.

(56) References Cited

U.S. PATENT DOCUMENTS

| 3,943,470 A | 3/1976 | Bingham |
| 4,116,202 A * | 9/1978 | Panicci ................. A61J 17/02 |
| | | 606/235 |

(Continued)

FOREIGN PATENT DOCUMENTS

| DE | 390937 C | 3/1924 |
| DE | 1099658 B | 2/1961 |

(Continued)

OTHER PUBLICATIONS

Search Report EP 98958575.7 dated Oct. 29, 2002.

(Continued)

*Primary Examiner* — Daniel W Fowler

(57) ABSTRACT

A dielectric spacer for use during microwave ablation of tissue is disclosed. The dielectric spacer includes a housing having a predetermined thickness and a skin-contacting bottom surface. The housing is configured to be filled with a dielectric material having a predetermined dielectric permittivity. The housing is further configured to be placed on the tissue in proximity with at least one microwave antenna assembly, wherein the thickness and the dielectric permittivity are configured to shift a maximum voltage standing wave ratio of the at least one microwave antenna assembly.

6 Claims, 5 Drawing Sheets

(56) References Cited

U.S. PATENT DOCUMENTS

| | | | |
|---|---|---|---|
| 4,557,272 A | 12/1985 | Carr | |
| 4,566,454 A | 1/1986 | Mehl et al. | |
| 4,658,836 A | 4/1987 | Turner | |
| 4,662,383 A * | 5/1987 | Sogawa | A61B 18/18 607/133 |
| 4,672,980 A | 6/1987 | Turner | |
| 4,700,716 A | 10/1987 | Kasevich et al. | |
| 4,776,086 A | 10/1988 | Kasevich et al. | |
| 4,800,899 A | 1/1989 | Elliott | |
| 4,934,365 A | 6/1990 | Morgenthaler | |
| 5,097,846 A | 3/1992 | Larsen | |
| 5,334,193 A | 8/1994 | Nardella | |
| 5,496,271 A * | 3/1996 | Burton | A61B 18/18 604/101.05 |
| 5,549,639 A | 8/1996 | Ross | |
| 5,800,432 A | 9/1998 | Swanson | |
| 5,904,709 A | 5/1999 | Arndt et al. | |
| 5,961,871 A | 10/1999 | Bible et al. | |
| 6,019,757 A | 2/2000 | Scheldrup | |
| 6,026,331 A | 2/2000 | Feldberg et al. | |
| 6,134,476 A | 10/2000 | Arndt et al. | |
| 6,175,768 B1 | 1/2001 | Arndt et al. | |
| 6,230,060 B1 | 5/2001 | Mawhinney | |
| 6,245,062 B1 | 6/2001 | Berube et al. | |
| 6,283,959 B1 * | 9/2001 | Lalonde | A61B 18/02 606/21 |
| 6,287,302 B1 | 9/2001 | Berube | |
| 6,334,074 B1 | 12/2001 | Spertell | |
| 6,336,926 B1 * | 1/2002 | Goble | A61B 17/3423 606/34 |
| 6,347,251 B1 | 2/2002 | Deng | |
| 6,398,781 B1 | 6/2002 | Goble et al. | |
| 6,690,959 B2 | 2/2004 | Thompson | |
| 6,723,091 B2 | 4/2004 | Goble et al. | |
| 6,847,848 B2 | 1/2005 | Sterzer et al. | |
| 7,070,595 B2 | 7/2006 | Ormsby et al. | |
| 7,101,369 B2 | 9/2006 | van der Welde | |
| 7,300,436 B2 | 11/2007 | Penny et al. | |
| 7,749,011 B2 | 7/2010 | Arts et al. | |
| 7,863,984 B1 | 1/2011 | Behnke | |
| 8,035,570 B2 | 10/2011 | Prakash et al. | |
| 8,059,059 B2 | 11/2011 | Bonn | |
| 8,118,808 B2 | 2/2012 | Smith et al. | |
| 8,182,480 B2 | 5/2012 | Huseman | |
| 8,192,427 B2 | 6/2012 | Buysse | |
| 8,197,473 B2 | 6/2012 | Rossetto et al. | |
| 8,202,270 B2 | 6/2012 | Rossetto et al. | |
| 8,211,098 B2 | 7/2012 | Paulus | |
| 8,216,227 B2 | 7/2012 | Podhajsky | |
| 8,221,418 B2 | 7/2012 | Prakash et al. | |
| 8,235,981 B2 | 8/2012 | Prakash et al. | |
| 8,251,987 B2 | 8/2012 | Willyard | |
| 8,292,881 B2 | 10/2012 | Brannan et al. | |
| 8,328,799 B2 | 12/2012 | Brannan | |
| 8,328,800 B2 | 12/2012 | Brannan | |
| 8,328,801 B2 | 12/2012 | Brannan | |
| 8,334,812 B2 | 12/2012 | Brannan | |
| 8,343,149 B2 | 1/2013 | Rossetto et al. | |
| 8,353,903 B2 | 1/2013 | Podhajsky | |
| 8,355,803 B2 | 1/2013 | Bonn et al. | |
| 8,394,086 B2 | 3/2013 | Behnke et al. | |
| 8,409,187 B2 | 4/2013 | Bonn | |
| 8,463,396 B2 | 6/2013 | Podhajsky | |
| 8,512,328 B2 | 8/2013 | Rossetto et al. | |
| 8,552,915 B2 | 10/2013 | Brannan | |
| 8,834,409 B2 | 9/2014 | Manley | |
| 8,834,460 B2 | 9/2014 | Peterson | |
| 9,031,668 B2 | 5/2015 | DeCarlo | |
| 9,095,359 B2 | 8/2015 | Behnke, II et al. | |
| 9,113,624 B2 | 8/2015 | Belous et al. | |
| 9,113,924 B2 | 8/2015 | Brannan et al. | |
| 9,113,925 B2 | 8/2015 | Smith et al. | |
| 9,113,926 B2 | 8/2015 | Brannan et al. | |
| 2002/0120261 A1 | 8/2002 | Morris et al. | |
| 2006/0287649 A1 | 12/2006 | Ormsby et al. | |
| 2006/0289528 A1 | 12/2006 | Chiu et al. | |
| 2006/0293652 A1 | 12/2006 | van der Weide | |
| 2007/0185554 A1 * | 8/2007 | Appling | A61B 18/18 607/101 |
| 2007/0203551 A1 | 8/2007 | Cronin et al. | |
| 2007/0233057 A1 | 10/2007 | Konishi | |
| 2008/0082090 A1 * | 4/2008 | Manstein | A61B 18/203 606/9 |
| 2008/0319434 A1 | 12/2008 | Rick et al. | |
| 2009/0306652 A1 | 12/2009 | Buysse et al. | |
| 2010/0030210 A1 | 2/2010 | Paulus | |
| 2010/0045558 A1 | 2/2010 | Rossetto | |
| 2010/0076422 A1 | 3/2010 | Podhajsky | |
| 2010/0094273 A1 | 4/2010 | Rossetto et al. | |
| 2010/0256624 A1 | 10/2010 | Brannan et al. | |
| 2010/0262134 A1 | 10/2010 | Jensen et al. | |
| 2011/0054458 A1 | 3/2011 | Behnke | |
| 2011/0054459 A1 | 3/2011 | Peterson | |
| 2011/0071511 A1 | 3/2011 | Brannan et al. | |

FOREIGN PATENT DOCUMENTS

| | | |
|---|---|---|
| DE | 1139927 B | 11/1962 |
| DE | 1149832 B | 6/1963 |
| DE | 1439302 A1 | 1/1969 |
| DE | 2439587 A1 | 2/1975 |
| DE | 2455174 A1 | 5/1975 |
| DE | 2407559 A1 | 8/1975 |
| DE | 2415263 A1 | 10/1975 |
| DE | 2429021 A1 | 1/1976 |
| DE | 2460481 A1 | 6/1976 |
| DE | 2602517 A1 | 7/1976 |
| DE | 2504280 A1 | 8/1976 |
| DE | 2627679 A1 | 1/1977 |
| DE | 2540968 A1 | 3/1977 |
| DE | 2820908 A1 | 11/1978 |
| DE | 2803275 A1 | 8/1979 |
| DE | 2823291 A1 | 11/1979 |
| DE | 2946728 A1 | 5/1981 |
| DE | 3143421 A1 | 5/1982 |
| DE | 3045996 A1 | 7/1982 |
| DE | 3120102 A1 | 12/1982 |
| DE | 3510586 A1 | 10/1986 |
| DE | 3604823 A1 | 8/1987 |
| DE | 8712328 U1 | 2/1988 |
| DE | 3711511 C1 | 6/1988 |
| DE | 3904558 A1 | 8/1990 |
| DE | 3942998 A1 | 7/1991 |
| DE | 4238263 A1 | 5/1993 |
| DE | 04303882 C2 | 2/1995 |
| DE | 4339049 A1 | 5/1995 |
| DE | 29616210 U1 | 11/1996 |
| DE | 19608716 C1 | 4/1997 |
| DE | 19751106 A1 | 5/1998 |
| DE | 19717411 A1 | 11/1998 |
| DE | 19751108 A1 | 5/1999 |
| DE | 19801173 C1 | 7/1999 |
| DE | 19848540 A1 | 5/2000 |
| DE | 10224154 A1 | 12/2003 |
| DE | 10328514 B3 | 3/2005 |
| DE | 102004022206 A1 | 12/2005 |
| DE | 202005015147 U1 | 2/2006 |
| EP | 0 246 350 A1 | 11/1987 |
| EP | 0 521 264 A2 | 1/1993 |
| EP | 0 556 705 A1 | 8/1993 |
| EP | 0 558 429 A1 | 9/1993 |
| EP | 0 836 868 A2 | 4/1998 |
| EP | 1159926 A3 | 3/2003 |
| FR | 179 607 | 11/1906 |
| FR | 1 275 415 A | 11/1961 |
| FR | 1 347 865 A | 1/1964 |
| FR | 2 235 669 A1 | 1/1975 |
| FR | 2 276 027 A1 | 1/1976 |
| FR | 2 313 708 A1 | 12/1976 |
| FR | 2 502 935 A1 | 10/1982 |
| FR | 2 517 953 A1 | 6/1983 |
| FR | 2 573 301 A1 | 5/1986 |
| FR | 2 862 813 A1 | 5/2005 |
| FR | 2 864 439 A1 | 7/2005 |

(56) References Cited

FOREIGN PATENT DOCUMENTS

| | | |
|---|---|---|
| JP | 5-5106 | 1/1993 |
| JP | 05-40112 | 2/1993 |
| JP | 06343644 A | 12/1994 |
| JP | 07265328 A | 10/1995 |
| JP | 08056955 | 3/1996 |
| JP | 08252263 A | 10/1996 |
| JP | 09010223 A | 1/1997 |
| JP | 11244298 A | 9/1999 |
| JP | 2000342599 A | 12/2000 |
| JP | 2000350732 A | 12/2000 |
| JP | 2001008944 A | 1/2001 |
| JP | 2001029356 A | 2/2001 |
| JP | 2001128990 A | 5/2001 |
| SU | 166452 | 1/1965 |
| SU | 401367 A1 | 10/1973 |
| SU | 727201 A2 | 4/1980 |

OTHER PUBLICATIONS

Search Report EP 03721482 dated Feb. 6, 2006.
Search Report EP 04009964 dated Jul. 28, 2004.
Search Report EP 04013772 dated Apr. 11, 2005.
Search Report EP 04015980 dated Nov. 3, 2004.
Search Report EP 04015981.6 dated Oct. 25, 2004.
Search Report EP 04027314 dated Mar. 31, 2005.
Search Report EP 04027479 dated Mar. 17, 2005.
Search Report EP 04027705 dated Feb. 10, 2005.
European Search Report EP 04710258 dated Oct. 15, 2004.
European Search Report EP 04752343.6 dated Jul. 31, 2007.
European Search Report EP 04778192.7 dated Jul. 1, 2009.
European Search Report EP 05002027.0 dated May 12, 2005.
European Search Report EP 05002769.7 dated Jun. 19, 2006.
European Search Report EP 05013463.4 dated Oct. 7, 2005.
European Search Report EP 05013895 dated Oct. 21, 2005.
European Search Report EP 05014156.3 dated Jan. 4, 2006.
European Search Report EP 05016399 dated Jan. 13, 2006.
European Search Report EP 05017281 dated Nov. 24, 2005.
European Search Report EP 05019130.3 dated Oct. 27, 2005.
European Search Report EP 05019882 dated Feb. 16, 2006.
European Search Report EP 05020665.5 dated Feb. 27, 2006.
European Search Report EP 05020666.3 dated Feb. 27, 2006.
European Search Report EP 05021025.1 dated Mar. 13, 2006.
European Search Report EP 05021197.8 dated Feb. 20, 2006.
European Search Report EP 05021777 dated Feb. 23, 2006.
European Search Report EP 05021779.3 dated Feb. 2, 2006.
European Search Report EP 05021780.1 dated Feb. 23, 2006.
European Search Report EP 05021935 dated Jan. 27, 2006.
European Search Report EP 05021936.9 dated Feb. 6, 2006.
European Search Report EP 05021937.7 dated Jan. 23, 2006.
European Search Report EP 05021939 dated Jan. 27, 2006.
European Search Report EP 05021944.3 dated Jan. 25, 2006.
European Search Report EP 05022350.2 dated Jan. 30, 2006.
European Search Report EP 05023017.6 dated Feb. 24, 2006.
European Search Report EP 05025423.4 dated Jan. 19, 2007.
European Search Report EP 05025424 dated Jan. 30, 2007.
European Search Report EP 05810523 dated Jan. 29, 2009.
European Search Report EP 06000708.5 dated May 15, 2006.
European Search Report EP 06002279.5 dated Mar. 30, 2006.
European Search Report EP 06005185.1 dated May 10, 2006.
European Search Report EP 06005540 dated Sep. 24, 2007.
European Search Report EP 06006717.0 dated Aug. 11, 2006.
European Search Report EP 06006961 dated Oct. 22, 2007.
European Search Report EP 06006963 dated Jul. 25, 2006.
European Search Report EP 06008779.8 dated Jul. 13, 2006.
European Search Report EP 06009435 dated Jul. 13, 2006.
European Search Report EP 06010499.9 dated Jan. 29, 2008.
European Search Report EP 06014461.5 dated Oct. 31, 2006.
European Search Report EP 06018206.0 dated Oct. 20, 2006.
European Search Report EP 09156861.8 dated Aug. 4, 2009.
European Search Report EP 09161502.1 dated Sep. 2, 2009.
European Search Report EP 09166708 dated Oct. 15, 2009.
International Search Report PCT/US98/18640 dated Jan. 29, 1998.
International Search Report PCT/US98/23950 dated Jan. 14, 1998.
International Search Report PCT/US99/24869 dated Feb. 11, 2000.
International Search Report PCT/US01/11218 dated Aug. 14, 2001.
International Search Report PCT/US01/11224 dated Nov. 13, 2001.
International Search Report PCT/US01/11340 dated Aug. 16, 2001.
International Search Report PCT/US01/11420 dated Oct. 16, 2001.
International Search Report PCT/US02/01890 dated Jul. 25, 2002.
International Search Report PCT/US02/11100 dated Jul. 16, 2002.
International Search Report PCT/US03/09483 dated Aug. 13, 2003.
International Search Report PCT/US03/22900 dated Dec. 2, 2003.
International Search Report PCT/US03/37110 dated Jul. 25, 2005.
International Search Report PCT/US03/37111 dated Jul. 28, 2004.
International Search Report PCT/US03/37310 dated Aug. 13, 2004.
International Search Report PCT/US04/04685 dated Aug. 27, 2004.
International Search Report PCT/US04/13273 dated Dec. 15, 2004.
International Search Report PCT/US04/15311 dated Jan. 12, 2004.
International Search Report PCT/US05/36168 dated Aug. 28, 2006.
International Search Report PCT/US08/052460 dated Apr. 24, 2008.
International Search Report PCT/US09/31658 dated Mar. 11, 2009.
European Search Report EP 06019768 dated Jan. 17, 2007.
European Search Report EP 06020574.7 dated Oct. 2, 2007.
European Search Report EP 06020583.8 dated Feb. 7, 2007.
European Search Report EP 06020584.6 dated Feb. 1, 2007.
European Search Report EP 06020756.0 dated Feb. 16, 2007.
European Search Report EP 06022028.2 dated Feb. 13, 2007.
European Search Report EP 06023756.7 dated Feb. 21, 2008.
European Search Report EP 06024122.1 dated Apr. 16, 2007.
European Search Report EP 06024123.9 dated Mar. 6, 2007.
European Search Report EP 06025700.3 dated Apr. 12, 2007.
European Search Report EP 07000885.9 dated May 15, 2007.
European Search Report EP 07001480.8 dated Apr. 19, 2007.
European Search Report EP 07001481.6 dated May 2, 2007.
European Search Report EP 07001485.7 dated May 23, 2007.
European Search Report EP 07001488.1 dated Jun. 5, 2007.
European Search Report EP 07001489.9 dated Dec. 20, 2007.
European Search Report EP 07001491 dated Jun. 6, 2007.
European Search Report EP 07001527.6 dated May 18, 2007.
European Search Report EP 07007783.9 dated Aug. 14, 2007.
European Search Report EP 07008207.8 dated Sep. 13, 2007.
European Search Report EP 07009026.1 dated Oct. 8, 2007.
European Search Report EP 07009028 dated Jul. 16, 2007.
European Search Report EP 07009029.5 dated Jul. 20, 2007.
European Search Report EP 07009321.6 dated Aug. 28, 2007.
European Search Report EP 07009322.4 dated Jan. 14, 2008.
European Search Report EP 07010672.9 dated Oct. 16, 2007.
European Search Report EP 07010673.7 dated Oct. 5, 2007.
European Search Report EP 07013779.9 dated Oct. 26, 2007.
European Search Report EP 07015191.5 dated Jan. 23, 2007.
European Search Report EP 07015601.3 dated Jan. 4, 2007.
European Search Report EP 07015602.1 dated Dec. 20, 2007.
European Search Report EP 07018375.1 dated Jan. 8, 2008.
European Search Report EP 07018821 dated Jan. 14, 2008.
European Search Report EP 07019173.9 dated Feb. 12, 2008.
European Search Report EP 07019174.7 dated Jan. 29, 2008.
European Search Report EP 07019178.8 dated Feb. 12, 2008.
European Search Report EP 07020283.3 dated Feb. 5, 2008.
European Search Report EP 07253835.8 dated Dec. 20, 2007.
European Search Report EP 08001019 dated Sep. 23, 2008.
European Search Report EP 08004975 dated Jul. 24, 2008.
European Search Report EP 08006731.7 dated Jul. 29, 2008.
European Search Report EP 08006733 dated Jul. 7, 2008.
European Search Report EP 08006734.1 dated Aug. 18, 2008.
European Search Report EP 08006735.8 dated Jan. 8, 2009.
European Search Report EP 08011282 dated Aug. 14, 2009.
European Search Report EP 08011705 dated Aug. 20, 2009.
European Search Report EP 08012829.1 dated Oct. 29, 2008.
European Search Report EP 08015842 dated Dec. 5, 2008.
European Search Report EP 08019920.1 dated Mar. 27, 2009.
European Search Report EP 08169973.8 dated Apr. 6, 2009.
U.S. Appl. No. 08/483,742, filed Jun. 7, 1995, Abandoned, Roger A. Stern.

(56) References Cited

OTHER PUBLICATIONS

U.S. Appl. No. 08/136,098, filed Oct. 14, 1993, Abandoned, Roger A. Stern.
U.S. Appl. No. 12/181,504, filed Jul. 29, 2008, Abandoned, Thomas A. Giuliani.
U.S. Appl. No. 12/197,601, filed Aug. 25, 2008, Abandoned, Thomas A. Giuliani.
U.S. Appl. No. 12/493,302, filed Jun. 29, 2009, Abandoned, Katherine Rodjom.
Alexander et al., "Magnetic Resonance Image-Directed Stereotactic Neurosurgery: Use of Image Fusion with Computerized Tomography to Enhance Spatial Accuracy" Journal Neurosurgery, 83 (1995), pp. 271-276.
Anderson et al., "A Numerical Study of Rapid Heating for High Temperature Radio Frequency Hyperthermia" International Journal of Bio-Medical Computing, 35 (1994), pp. 297-307.
Anonymous. (1999) Auto Suture MIBB Site Marker: Single Use Clip Applier, United States Surgical (Product instructions), 2 pages.
Anonymous. (2001) Disposable Chiba Biopsy Needles and Trays, Biopsy and Special Purpose Needles Cook Diagnostic and Interventional Products Catalog (products list), 4 pages.
Anonymous. (1987) Homer Mammalok.TM. Breast Lesion Needle/Wire Localizer, Namic.RTM. Angiographic Systems Division, Glens Falls, New York, (Hospital products price list), 4 pages.
Anonymous. (1999) MIBB Site Marker, United States Surgical (Sales brochure), 4 pages.
Anonymous. Blunt Tubes with Finished Ends. Pointed Cannula, Popper & Sons Biomedical Instrument Division, (Products Price List), one page, Jul. 19, 2000.
Anonymous. Ground Cannulae, ISPG, New Milford, CT, (Advertisement) one page, Jul. 19, 2000.
B. Levy M.D. et al., "Randomized Trial of Suture Versus Electrosurgical Bipolar Vessel Sealing in Vaginal Hysterectomy" Obstetrics & Gynecology, vol. 102, No. 1, Jul. 2003.
B. Levy M.D. et al., "Update on Hysterectomy New Technologies and Techniques" OBG Management, Feb. 2003.
B. Levy M.D., "Use of a New Vessel Ligation Device During Vaginal Hysterectomy" FIGO 2000, Washington, D.C.
B. F. Mullan et al., (May 1999) "Lung Nodules: Improved Wire for CT-Guided Localization," Radiology 211:561-565.
B. T. Heniford M.D. et al., "Initial Research and Clinical Results with an Electrothermal Bipolar Vessel Sealer" Oct. 1999.
Bergdahl et al., "Studies on Coagulation and the Development of an Automatic Computerized Bipolar Coagulator" Journal of Neurosurgery 75:1 (Jul. 1991), pp. 148-151.
Bulletin of the American Physical Society, vol. 47, No. 5, Aug. 2002, p. 41.
C. F. Gottlieb et al., "Interstitial Microwave Hyperthermia Applicators having Submillimetre Diameters", Int. J. Hyperthermia, vol. 6, No. 3, pp. 707-714, 1990.
C. H. Dumey et al., "Antennas for Medical Applications", Antenna Handbook: Theory Application and Design, p. 24-40, Van Nostrand Reinhold, 1988 New York, V.T. Lo, S.W. Lee.
Carbonell et al., "Comparison of the Gyrus PlasmaKinetic Sealer and the Valleylab LigaSure.TM. Device in the Hemostasis of Small, Medium, and Large-Sized Arteries" Carolinas Laparoscopic and Advanced Surgery Program, Carolinas Medical Center,Charlotte, NC 2003.
Carus et al., "Initial Experience With the LigaSure.TM. Vessel Sealing System in Abdominal Surgery" Innovations That Work, Jun. 2002.
Chicharo et al., "A Sliding Goertzel Algorithm" Aug. 1996 DOS pp. 283-297 Signal Processing, Elsevier Science Publishers B.V. Amsterdam, NL, vol. 52, No. 3.
Chou, C.K., (1995) "Radiofrequency Hyperthermia in Cancer Therapy," Chapter 94In Biologic Effects of Nonionizing Electromagnetic Fields, CRC Press, Inc., pp. 1424-1428.
Chung et al., "Clinical Experience of Sutureless Closed Hemorrhoidectomy with LigaSure.TM." Diseases of the Colon & Rectum, vol. 46, No. 1, Jan. 2003.

Cosman et al., "Methods of Making Nervous System Lesions" In William RH, Rengachary SS (eds): Neurosurgery, New York: McGrawHill, vol. 111, (1984), pp. 2490-2499.
Cosman et al., "Radiofrequency Lesion Generation and its Effect on Tissue Impedence", Applied Neurophysiology, 51:230-242, 1988.
Cosman et al., "Theoretical Aspects of Radiofrequency Lesions in the Dorsal Root Entry Zone" Neurosurgery 15: (1984), pp. 945-950.
Crawford et al., "Use of the LigaSure.TM. Vessel Sealing System in Urologic Cancer Surger" Grand Rounds in Urology 1999, vol. 1, Issue 4, pp. 10-17.
Dulemba et al., "Use of a Bipolar Electrothermal Vessel Sealer in Laparoscopically Assisted Vaginal Hysterectomy" Sales/Product Literature; Jan. 2004.
E. David Crawford, "Evaluation of a New Vessel Sealing Device in Urologic Cancer Surgery" Sales/Product Literature 2000.
E. David Crawford, "Use of a Novel Vessel Sealing Technology in Management of the Dorsal Veinous Complex" Sales/Product Literature 2000.
Esterline, "Light Key Projection Keyboard" 2004 Advanced Input Systems, located at: <http://www.advanced-input.com/lightkey> last visited on Feb. 10, 2005.
Esterline Product Literature, "Light Key: Visualize a Virtual Keyboard. One With No Moving Parts", Nov. 1, 2003; 4 pages.
Geddes et al., "The Measurement of Physiologic Events by Electrical Impedence" Am. J. MI, Jan. Mar. 1964, pp. 16-27.
Goldberg et al., "Image-guided Radiofrequency Tumor Ablation: Challenges and Opportunities—Part I", (2001) J Vasc. Interv. Radiol, vol. 12, pp. 1021-1032.
Goldberg et al., "Tissue Ablation with Radiofrequency: Effect of Probe Size, Gauge, Duration, and Temperature on Lesion Volume" Acad Radio (1995) vol. 2, No. 5, pp. 399-404.
H. Schwarzmaier et al., "Magnetic Resonance Imaging of Microwave Induced Tissue Heating" Dept. of Laser Medicine & Dept. of Diagnostic Radiology; Heinrich-Heine-University, Duesseldorf, Germany; Dec. 8, 1994; pp. 729-731.
Heniford et al., "Initial Results with an Electrothermal Bipolar Vessel Sealer" Surgical Endoscopy (2001) 15:799-801.
Herman at al., "Laparoscopic Intestinal Resection With the LigaSure.TM. Vessel Sealing System: A Case Report" Innovations That Work, Feb. 2002.
Humphries Jr. et al., "Finite.Element Codes to Model Electrical Heating and Non.cndot.LInear Thermal Transport in Biological Media", Proc. ASME HTD-355, 131 (1997).
Ian D. McRury et al., The Effect of Ablation Sequence and Duration on Lesion Shape Using Rapidly Pulsed Radiofrequency Energy Through Electrodes, Feb. 2000, Springer Netherlands, vol. 4; No. 1, pp. 307-320.
Jarrett et al., "Use of the LigaSure.TM. Vessel Sealing System for Peri-Hilar Vessels in Laparoscopic Nephrectomy" Sales/Product Literature 2000.
Johnson et al., "Evaluation of a Bipolar Electrothermal Vessel Sealing Device in Hemorrhoidectomy" Sales/Product Literature, Jan. 2004.
Johnson, "Evaluation of the LigaSure.TM. Vessel Sealing System in Hemorrhoidectormy" American College of Surgeons (ACS) Clinic La Congress Poster (2000).
Johnson, "Use of the LigaSure.TM. Vessel Sealing System in Bloodless Hemorrhoidectomy" Innovations That Work, Mar. 2000.
Joseph G. Andriole M.D. et al., "Biopsy Needle Characteristics Assessed in the Laboratory", Radiology 148: 659-662, Sep. 1983.
Joseph Ortenberg, "LigaSure.TM. System Used in Laparoscopic 1st and 2nd Stage Orchiopexy" Innovations That Work, Nov. 2002.
K. Ogata, Modern Control Engineering, Prentice-Hall, Englewood Cliffs, N.J., 1970.
Kennedy et al., "High-burst-strength, feedback-controlled bipolar vessel sealing" Surgical Endoscopy (1998) 12: 876-878.
Kopans, D.B. et al., (Nov. 1985) "Spring Hookwire Breast Lesion Localizer: Use with Rigid-Compression. Mammographic Systems," Radiology 157(2):537-538.
Koyle et al., "Laparoscopic Palomo Varicocele Ligation in Children and Adolescents" Pediatric Endosurgery & Innovative Techniques, vol. 6, No. 1, 2002.

(56) References Cited

OTHER PUBLICATIONS

LigaSure.TM. Vessel Sealing System, the Seal of Confidence in General, Gynecologic, Urologic, and Laparaoscopic Surgery, Sales/Product Literature, Jan. 2004.
Livraghi et al., (1995) "Saline-enhanced RF Tissue Ablation in the Treatment of Liver Metastases", Radiology, pp. 205-210.
Lyndon B. Johnson Space Center, Houston, Texas, "Compact Directional Microwave Antenna for Localized Heating," NASA Tech Briefs, Mar. 2008.
M. A. Astrahan, "A Localized Current Field Hyperthermia System for Use with 192-Iridium Interstitial Implants" Medical Physics. 9(3), May/Jun. 1982.
Magdy F. Iskander et al., "Design Optimization of Interstitial Antennas", IEEE Transactions on Biomedical Engineering, vol. 36, No. 2, Feb. 1989, pp. 238-246.
McGahan et al., (1995) "Percutaneous Ultrasound-guided Radiofrequency Electrocautery Ablation of Prostate Tissue in Dogs", Acad Radial, vol. 2, No. 1: pp. 61-65.
McLellan et al., "Vessel Sealing for Hemostasis During Pelvic Surgery" Int'l Federation of Gynecology and Obstetrics Figo World Congress 2000, Washington, DC.
MDTECH product literature (Dec. 1999) "FlexStrand": product description, 1 page.
MDTECH product literature (Mar. 2000) I'D Wire: product description, 1 page.
Medtrex Brochure "The O.R. Pro 300" 1 page, Sep. 1998.
Michael Choti, "Abdominoperineal Resection with the LigaSure. TM. Vessel Sealing System and LigaSure.TM. Atlas 20 cm Open Instrument" Innovations That Work, Jun. 2003.
Muller et al., "Extended Left Hemicolectomy Using the LigaSure. TM. Vessel Sealing System" Innovations That Work. LJ, Sep. 1999.
Murakami, R. et al., (1995). "Treatment of Hepatocellular Carcinoma: Value of Percutaneous Microwave Coagulation," American Journal of Radiology (AJR) 164:1159-1164.
Ni Wei et al., "A Signal Processing Method for the Coriolis Mass Flowmeter Based on a Normalized . . . " Journal of Applied Sciences.cndot.Yingyong Kexue Xuebao, Shanga CN, vol. 23, No. 2:(Mar. 2005); pp. 160-184.
Ogden, "Goertzel Alternative to the Fourier Transform" Jun. 1993 pp. 485-487 Electronics World; Reed Business Publishing, Sutton, Surrey, BG, vol. 99, No. 9, 1687.
Olsson M.D. et al., "Radical Cystectomy in Females" Current Surgical Techniques in Urology, vol. 14, Issue 3, 2001.
Organ, L W., "Electrophysiologic Principles of Radiofrequency Lesion Making" Appl. Neurophysiol, vol. 39: pp. 69-76 (1976/77).
P.R. Stauffer et al., "Interstitial Heating Technologies", Thermoradiotheray and Thermochemotherapy (1995) vol. I. Biology, Physiology, Physics, pp. 279-320.
Palazzo et al., "Randomized clinical trial of LigaSure.TM. versus open haemorrhoidectomy" British Journal of Surgery 2002,89,154-157 "Innovations in Electrosurgery" Sales/Product Literature; Dec. 31, 2000.
Paul G. Horgan, "A Novel Technique for Parenchymal Division During Hepatectomy" The American Journal of Surgery, vol. 181, No. 3, Apr. 2001, pp. 236-237.
Peterson et al., "Comparison of Healing Process Following Ligation with Sutures and Bipolar Vessel Sealing" Surgical Technology International (2001).

R. Gennari et al., (Jun. 2000) "Use of Technetium-99m-Labeled Colloid Albumin for Preoperative and Intraoperative Localization of Non palpable Breast Lesions," American College of Surgeons. 190(6):692-699.
Valleylab Brochure, "Reducing Needlestick Injuries in the Operating Room" 1 page, Mar. 2001.
Reidenbach, (1995) "First Experimental Results with Special Applicators for High-Frequency Interstitial Thermotherapy", Society Minimally Invasive Therapy, 4(Suppl 1):40 (Abstr).
Richard Wolf Medical Instruments Corp. Brochure, "Kleppinger Bipolar Forceps & Bipolar Generator" 3 pages, Jan. 1989.
Rothenberg et al., "Use of the LigaSure.TM. Vessel Sealing System in Minimally Invasive Surgery in Children" Int'l Pediatric Endosurgery Group (I PEG) 2000.
Sayfan et al., "Sutureless Closed Hemorrhoidectomy: A New Technique" Annals of Surgery, vol. 234, No. 1, Jul. 2001, pp. 21-24.
Sengupta et al., "Use of a Computer-Controlled Bipolar Diathermy System in Radical Prostatectomies and Other Open Urological Surgery" ANZ Journal of Surgery (2001)71.9 pp. 538-540.
Sigel et al., "The Mechanism of Blood Vessel Closure by High Frequency Electrocoagulation" Surgery Gynecology & Obstetrics, Oct. 1965 pp. 823-831.
Solbiati et al., (2001) "Percutaneous Radio-frequency Ablation of Hepatic Metastases from Colorectal Cancer: Long-term Results in 117 Patients", Radiology, vol. 221, pp. 159-166.
Strasberg et al., "Use of a Bipolar Vassel-Sealing Device for Parenchymal Transection During Liver Surgery" Journal of Gastrointestinal Surgery, vol. 6, No. 4, Jul./Aug. 2002 pp. 569-574.
Stuart W. Young, Nuclear Magnetic Resonance Imaging—Basic Principles, Raven Press, New York, 1984.
Sugita et al., "Bipolar Coagulator with Automatic Thermocontrol" J. Neurosurg., vol. 41, Dec. 1944, pp. 777-779.
Sylvain Labonte et al., "Monopole Antennas for Microwave Catheter Ablation", IEEE Trans. on Microwave Theory and Techniques, vol. 44, No. 10, pp. 1832-1840, Oct. 1995.
T. Matsukawa et al., "Percutaneous Microwave Coagulation Therapy in Liver Tumors", Acta Radiologica, vol. 38, pp. 410-415, 1997.
T. Seki et al., (1994) "Ultrasonically Guided Percutaneous Microwave Coagulation Therapy for Small Hepatocellular Carcinoma," Cancer 74(3):817.cndot.825.
Urologix, Inc.—Medical Professionals: Targis.TM. Technology (Date Unknown). "Overcoming the Challenge" located at: <http://www.urologix.com!medicaUtechnology.html > last visited on Apr. 27, 2001, 3 pages.
Urrutia et al., (1988). "Retractable-Barb Needle for Breast Lesion Localization: Use in 60 Cases," Radiology 169 (3):845-847.
Valleylab Brochure, "Valleylab Electroshield Monitoring System" 2 pages, Nov. 1995.
ValleyLab Brochure, "Electosurgery: A Historical Overview", Innovations in Electrosurgery, 1999.
Vallfors et al., "Automatically Controlled Bipolar Electrocoagulation—'COA-COMP'" Neurosurgical Review 7:2-3 (1984) pp. 187-190.
W. Scott Helton, "LigaSure.TM. Vessel Sealing System: Revolutionary Hemostasis Product for General Surgery" Sales/Product Literature 1999.
Wald et al., "Accidental Burns", JAMA, Aug. 16, 1971, vol. 217, No. 7, pp. 916-921.
Walt Boyles, "Instrumentation Reference Book", 2002, Butterworth-Heinemann, pp. 262-264.
European Search Report EP 98300964.8 dated Dec. 13, 2000.
European Search Report EP 98944778 dated Nov. 7, 2000.

\* cited by examiner

MANAGEMENT OF VOLTAGE STANDING WAVE RATIO AT SKIN SURFACE DURING MICROWAVE ABLATION

CROSS-REFERENCE TO RELATED APPLICATIONS

This application is a continuation application of U.S. patent application Ser. No. 12/568,883 filed on Sep. 29, 2009, the entire contents of which is incorporated herein by reference.

BACKGROUND

1. Technical Field

The present disclosure relates generally to microwave antennas. More particularly, the present disclosure is directed to systems and methods for shifting voltage standing wave ratio at the tissue surface to reduce the amount microwave energy being deposited at the surface.

2. Background of Related Art

Treatment of certain diseases requires destruction of malignant tissue growths (e.g., tumors). It is known that tumor cells denature at elevated temperatures that are slightly lower than temperatures injurious to surrounding healthy cells. Therefore, known treatment methods, such as hyperthermia therapy, heat tumor cells to temperatures above 41° C., while maintaining adjacent healthy cells at lower temperatures to avoid irreversible cell damage. Such methods involve applying electromagnetic radiation to heat tissue and include ablation and coagulation of tissue. In particular, microwave energy is used to coagulate and/or ablate tissue to denature or kill the cancerous cells.

Microwave energy is applied via microwave ablation antennas that penetrate tissue to reach tumors. There are several types of microwave antennas, such as monopole and dipole, in which microwave energy radiates perpendicularly from the axis of the conductor. A monopole antenna includes a single, elongated microwave conductor whereas a dipole antenna includes two conductors. In a dipole antenna, the conductors may be in a coaxial configuration including an inner conductor and an outer conductor separated by a dielectric portion. More specifically, dipole microwave antennas may have a long, thin inner conductor that extends along a longitudinal axis of the antenna and is surrounded by an outer conductor. In certain variations, a portion or portions of the outer conductor may be selectively removed to provide more effective outward radiation of energy. This type of microwave antenna construction is typically referred to as a "leaky waveguide" or "leaky coaxial" antenna.

Conventional microwave antennas operate at a single frequency allowing for creation of similarly shaped lesions (e.g., spherical, oblong, etc.). Some antennas are capable of radiating energy inside as well as outside tissue, due to well-tuned impedance matching. In some instances this may result in inadvertent radiation at the tissue surface.

SUMMARY

According to one embodiment of the present disclosure, a dielectric spacer for use during microwave ablation of tissue is disclosed. The dielectric spacer includes a housing having a predetermined thickness and a skin-contacting bottom surface. The housing is configured to be filled with a dielectric material having a predetermined dielectric permittivity. The housing is further configured to be placed on the tissue in proximity with at least one microwave antenna assembly, wherein the thickness and the dielectric permittivity are configured to shift a maximum voltage standing wave ratio of the at least one microwave antenna assembly.

According to another embodiment of the present disclosure, a dielectric spacer for use during microwave ablation of tissue is disclosed. The dielectric spacer includes a gel layer formed from a dielectric, elastic, shape-memory gel. The dielectric spacer also includes first and second substrates selected from at least one of film and foam and formed from a dielectric polymer. The first substrate is disposed on a top surface of the gel layer and the second substrate is disposed on a bottom surface of the gel layer, wherein the gel layer and the first and second substrates are configured to be perforated by at least one antenna assembly.

According to a further embodiment of the present disclosure a dielectric spacer for use during microwave ablation of tissue is disclosed. The dielectric spacer includes an inflatable, conformable housing having a skin-contacting bottom surface and configured to be inflated to a predetermined thickness. The housing is configured to be filled with a dielectric material having a predetermined dielectric permittivity. The housing is further configured to be placed on the tissue in proximity with at least one microwave antenna assembly, wherein the thickness and the dielectric permittivity are configured to shift a maximum voltage standing wave ratio of the at least one microwave antenna assembly.

BRIEF DESCRIPTION OF THE DRAWINGS

The above and other aspects, features, and advantages of the present disclosure will become more apparent in light of the following detailed description when taken in conjunction with the accompanying drawings in which.

DETAILED DESCRIPTION

Particular embodiments of the present disclosure are described herein below with reference to the accompanying drawings. In the following description, well-known functions or constructions are not described in detail to avoid obscuring the present disclosure in unnecessary detail.

Figure 1:
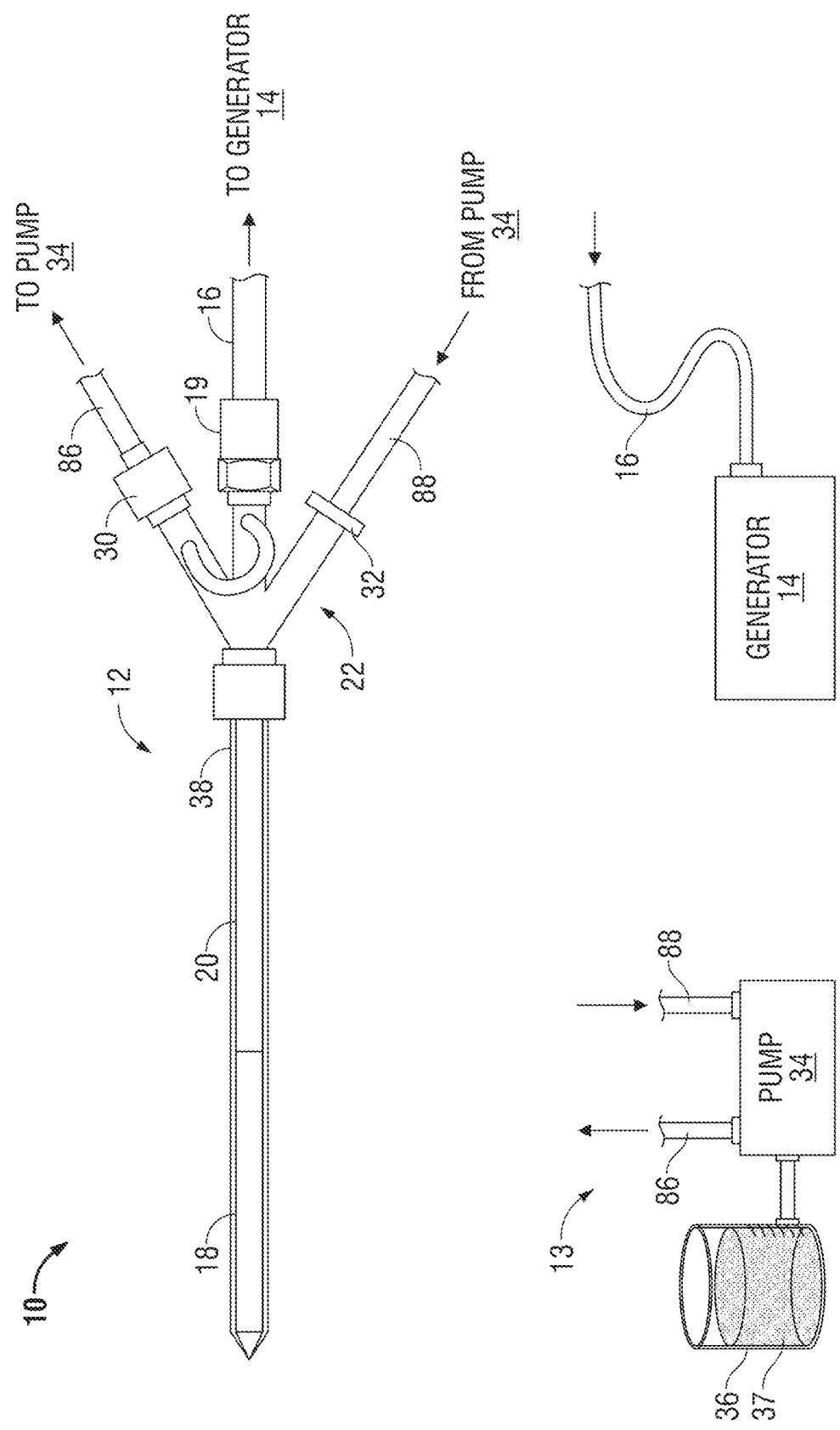
FIG. 1 is a schematic diagram of an ablation system according to the present disclosure.

FIG. 1 shows a microwave ablation system 10 that includes a microwave antenna assembly 12 coupled to a microwave generator 14 via a flexible coaxial cable 16. The generator 14 is configured to provide microwave energy at an operational frequency from about 500 MHz to about 10,000 MHz. In the illustrated embodiment, the antenna assembly 12 includes a radiating section 18 connected by feedline 20 (or shaft) to the cable 16. The feedline 20 may be connected to a hub 22, which is connected to the cable 16 through a cable connector 19. The hub 22 may have a variety of suitable shapes, e.g., cylindrical, rectangular, etc.

The feedline 20 may be coaxial and may include an inner conductor surrounded by an inner insulator, which is, in turn, surrounded by an outer conductor (e.g., a cylindrical conducting sheath). The inner and outer conductors are coupled to the cable 16 via the connector 19. The inner conductor and outer conductor may be constructed of copper, gold, stainless steel or other conductive metals with similar conductivity values. The metals may be plated with other materials, e.g., other conductive materials, to improve their properties, e.g., to improve conductivity or decrease energy loss, etc. In one embodiment, the feedline 20 may be formed from a coaxial, semi-rigid or flexible cable having a wire with a 0.047" outer diameter rated for 50 Ohms.

The connection hub 22 also couples the antenna assembly 12 to a cooling system 13. The connection hub 22 includes an outlet fluid port 30 and an inlet fluid port 32 that are connected in fluid communication with a sheath 38. The sheath 38 encloses radiating portion 18 and feedline 20 allowing a coolant fluid 37 to circulate from ports 30 and 32 around the antenna assembly 12. The ports 30 and 32 are also coupled to a supply pump 34 that is, in turn, coupled to a supply tank 36 via supply lines 86 and 88, respectively. The supply pump 34 may be a peristaltic pump or any other suitable type. The supply tank 36 stores the coolant fluid 37 and, in one embodiment, may maintain the fluid at a predetermined temperature. More specifically, the supply tank 36 may include a coolant unit that cools the returning liquid from the antenna assembly 12. In another embodiment, the coolant fluid 37 may be a gas and/or a mixture of liquid and gas. The coolant fluid 37 provides for dielectric impedance buffering for the antenna assembly 12. This allows for radiation of significant amounts of power while the antenna assembly 12 is partially inserted in the tissue or exposed to air.

Figure 2:
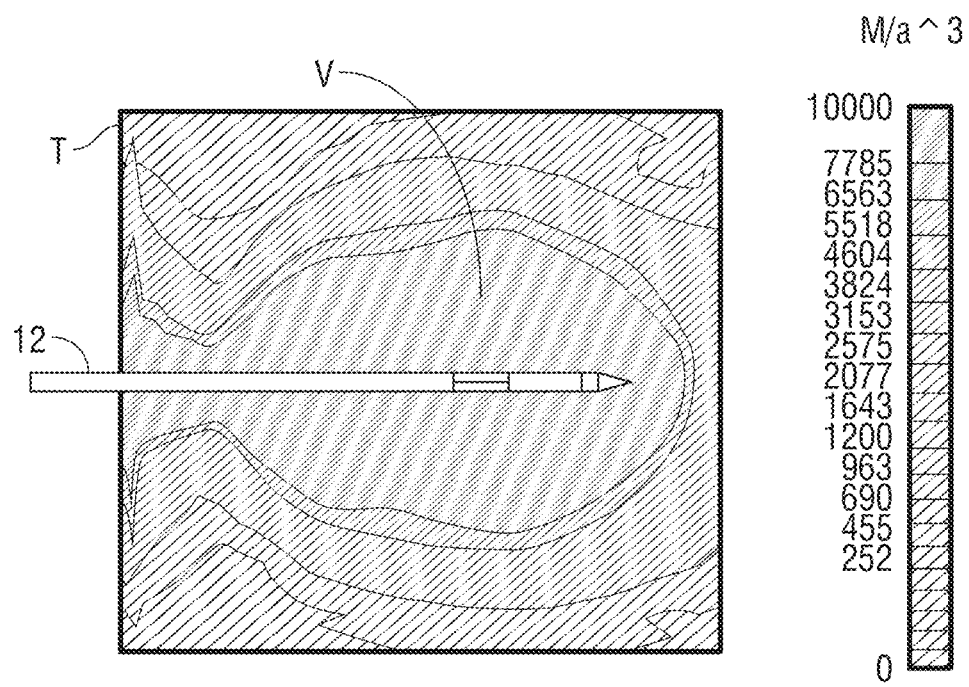
FIG. 2 is a cross-sectional view of an antenna assembly of FIG. 1 showing specific absorption rate with an unshifted voltage standing wave ratio according to the present disclosure.

During operation, one or more of the antenna assemblies 12 are inserted into tissue through the skin. In a percutaneous application, the interface between the air and the tissue at the insertion point determines the locations of voltage standing wave ratio ("VSWR") maximums along the transmission path. A VSWR maximum forms at the insertion point due to the dramatic change in impedance between air and tissue, significantly increasing the specific absorption rate ("SAR") when compared with VSWR minimums. FIG. 2 illustrates the SAR profile of the antenna assembly 12 being inserted in the tissue "T" having a VSWR maximum at the insertion point. This results in the increased radiation of microwave energy at the insertion point as illustrated by the ablation volume "V."

Figure 3:
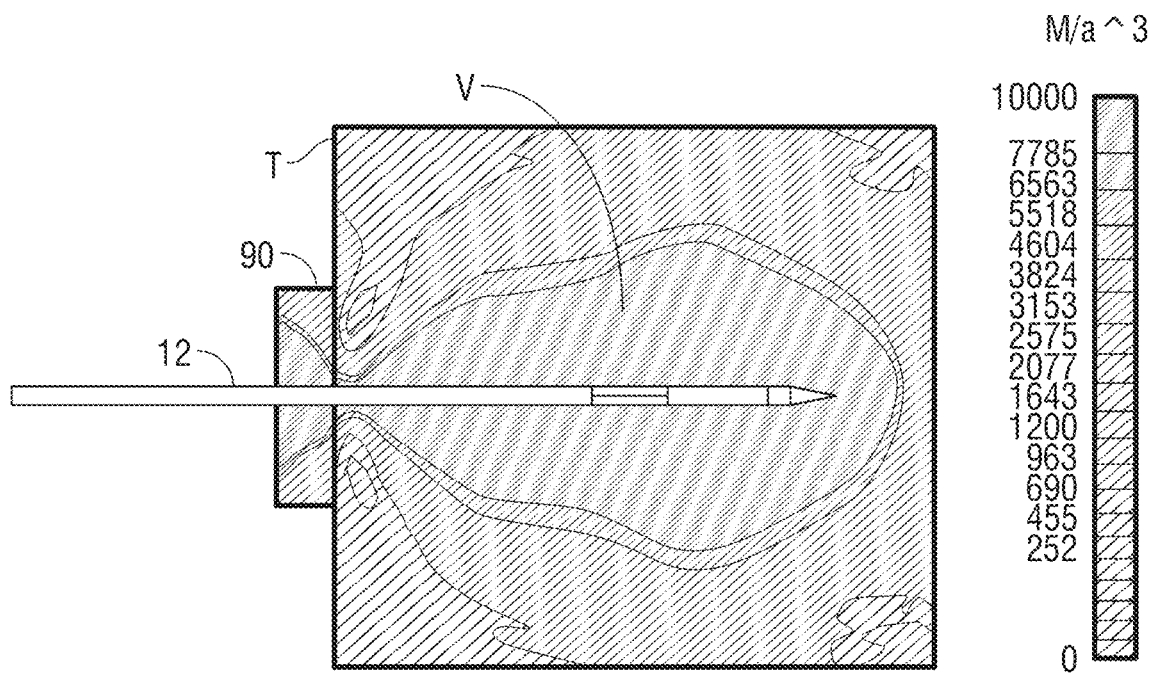
FIG. 3 is a cross-sectional view of an antenna assembly of FIG. 1 showing specific absorption rate with a shifted voltage standing wave ratio according to the present disclosure.

The present disclosure provides for a system and method of shifting the VSWR to effectively match the impedance of the tissue "T" on the surface thereof. This involves shifting the location of the VSWR maximum nearest the tissue surface into a material placed in proximity thereof. More specifically, the present disclosure provides for a dielectric spacer 90 (FIG. 4) formed from a material that matches the impedance of the tissue "T" allowing for the shifting of the VSWR and thereby spreading out the SAR profile as shown in FIG. 3. More specifically, the SAR is minimized at the surface of the tissue "T" due to the shift in VSWR maximum into the spacer 90. In addition, the VSWR minimum is shifted to the interface between the spacer 90 and the tissue "T," thereby minimizing the effects of microwave energy at the surface.

Figure 4:
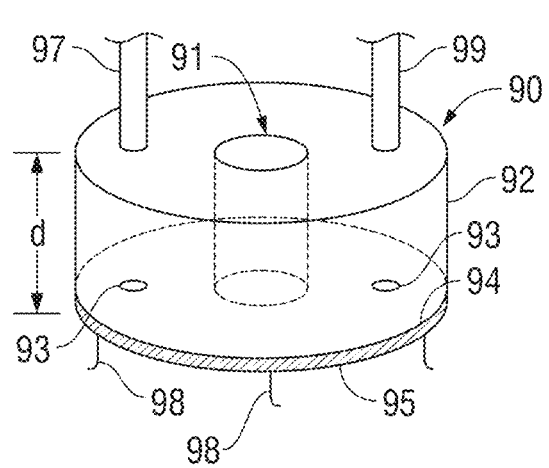
FIG. 4 is a perspective, cross-sectional view of a dielectric spacer according to one embodiment of the present disclosure.

FIG. 4 illustrates the dielectric spacer 90 having a substantially toroidal shape. The spacer 90 may be formed from a solid dielectric material having a dielectric permittivity from about 2 $\varepsilon_r$ to about 80 $\varepsilon_r$. The disclosed dielectric permittivity values are provide one illustrative embodiment and are dependant on the dimensions of the material (e.g., dielectric spacer 90) as well as the frequency of the energy supplied thereto and are thickness. The lower end of dielectric materials may include plastics, polymers (e.g., PTFE), and combination thereof. Upper end of dielectric material may include ceramics. In one embodiment, materials of various dielectric properties may be mixed (e.g., ceramic particles embedded in polymer gels). In another embodiment, the spacer 90 may include a rigid housing 92. The housing 92 has a predetermined thickness "d" that is selected based on the frequency of the microwave energy being supplied by the antenna assemblies 12 as well as the dielectric permittivity of the dielectric material of the spacer 90. The distance "d" is selected to shift the VSWR by the predetermined amount, such that the minimum VSWR is at the surface of the tissue "T."

The housing 92 may be filled with any suitable dielectric liquid or deformable material such as water, saline, dielectric gels, powders, etc. and mixtures thereof. If a dielectric liquid is used, the dielectric may be the coolant fluid 37. More specifically, the spacer 90 may be coupled to the cooling system 13 via supply lines 97 and 99, which may be directly coupled to the pump or may be integrated with the supply lines 86 and 88 of the antenna assembly 12.

In one embodiment, the spacer 90 may include one or more skin temperature monitoring devices 93, such as thermal probes, thermocouples, thermistors, optical fibers and the like, to monitor skin surface temperature. The temperature monitoring devices 93 are coupled to the cooling system 13 and provide the temperature measurements or indicators thereto. The cooling system 13 then controls the flow and the temperature (e.g., cooling) of the coolant fluid 37 based on the temperature measured at the surface of the tissue "T." In other words, the cooling system 13 increases the flow of the coolant fluid 37 and/or decreases the temperature of the coolant fluid 37 when the temperature of the tissue "T" increases and vice versa.

The spacer 90 also includes an aperture 91 defined therein for insertion of the antenna assembly 12 therethrough and into the tissue "T." The aperture 91 may be sized to be in frictional contact with the antenna assembly 12, thereby preventing movement of the antenna assembly 12 while allowing for relatively easier insertion therethrough.

The spacer 90 may also include one or more fastening elements 98 disposed on a skin-contacting bottom surface 94. The elements 98 may be hooks, barbs and other tissue-penetrating elements suitable for retaining the spacer 90. The spacer 90 may also include an adhesive layer 95 disposed on the bottom surface 94 thereof. In one embodiment, a protective film may be disposed over the adhesive layer 95 to protect the adhesive prior to use.

Figure 5:
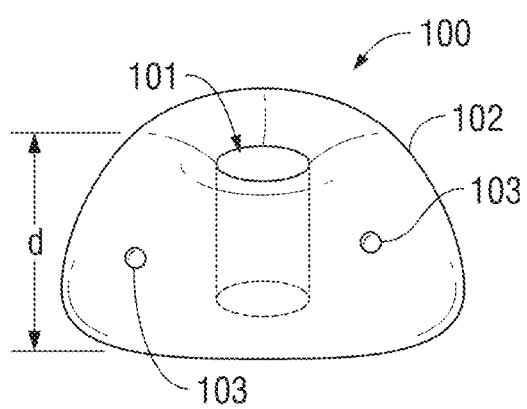
FIG. 5 is a perspective, cross-sectional view of a dielectric spacer according to another embodiment the present disclosure.

FIG. 5 shows another embodiment of a dielectric spacer 100 which is shaped as a bolus having a flexible expandable housing 102. The housing 102 includes an aperture 101 defined therein for insertion of the antenna assembly 12 therethrough and into the tissue "T." The aperture 101 may be sized to be in frictional contact with the antenna assembly 12 thereby preventing movement of the antenna assembly 12 while allowing for relatively easier insertion. The housing 102 may be filled with any suitable dielectric liquid or deformable material such as water, saline, dielectric gels, and mixtures thereof. If a dielectric liquid is utilized, the housing 102 may be coupled to the coolant system 13 to provide for circulation of the coolant fluid 37 and may also include one or more temperature monitoring devices (not explicitly shown) to provide for temperature-based cooling thereof as described above with respect to the spacer 90.

In one embodiment, the spacer 100 may include one or more skin temperature monitoring devices 103 disposed internally or externally, such as thermal probes, thermocouples, thermistors, optical fibers and the like, to monitor skin surface temperature. The temperature monitoring devices 103 are coupled to the cooling system 13 and provide the temperature measurements or indicators thereto. The cooling system 13 then controls the flow and the temperature (e.g., cooling) of the coolant fluid 37 based on the temperature measured at the surface of the tissue "T." In other words, the cooling system 13 increases the flow of the coolant fluid 37 and/or decreases the temperature of the coolant fluid 37 when the temperature of the tissue "T" increases and vice versa.

The flexible expandable structure of the housing 102 allows the spacer 100 to conform to the tissue. The conforming nature of the spacer 100 allows for the inflation of the spacer 100 to desired dimensions, namely, to a predetermined thickness "d" that is selected based on the frequency of the microwave energy being supplied by the antenna assemblies 12. The distance "d" is selected to shift the VSWR by the predetermined amount, such that the minimum VSWR is at the surface of the tissue "T." In addition, the conforming nature of the housing 102 allows the aperture 101 to be shifted within the spacer 100 to provide for various angles of insertion of the antenna assembly 12 therethrough.

Figure 6:
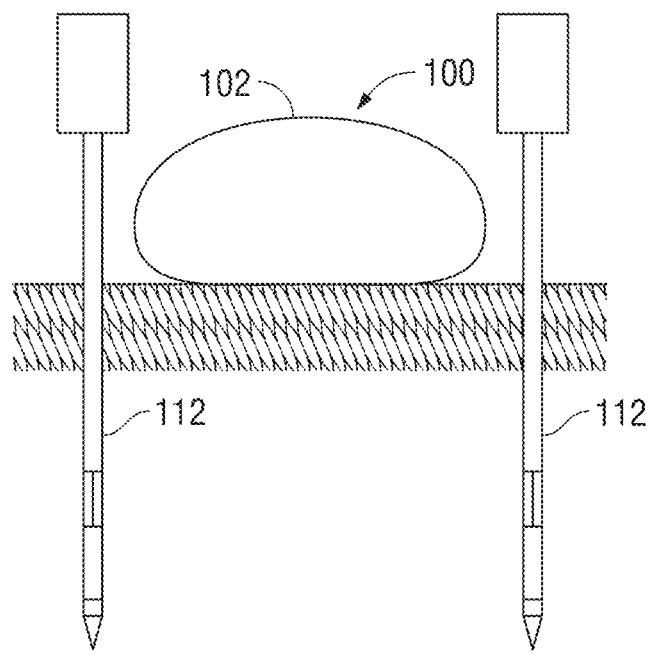
FIG. 6 is a side, cross-sectional view of a dielectric spacer according to a further embodiment the present disclosure.

In another embodiment, the spacer 100 may be used with multiple probes, which obviates the need for the aperture 101. The spacer 100 may be placed in proximity of (e.g., between) a plurality of antenna assemblies 12 as shown in FIG. 6. Ablations involving multiple probes, namely, simultaneous application of microwave energy through a plurality of antenna assemblies 12 provide additional risk of VSWR occurrence. In other words, a VSWR maximum occurs at the tissue-air boundary around and between the antenna assemblies 12, which has the potential to cause skin burns in high-power and/or long-duration microwave applications. Ablations using a plurality of antenna assemblies 12 are particularly susceptible to causing high power absorption rates near the surface due to the potential for so-called "two-wire" line energy propagation from the radiating sections 18. Thus, placement of the spacer 100 between the plurality of antenna assemblies 12 shifts the VSWR maximum away from the surface of the tissue "T" as shown in FIG. 3 and described above with respect thereto.

Figure 7:
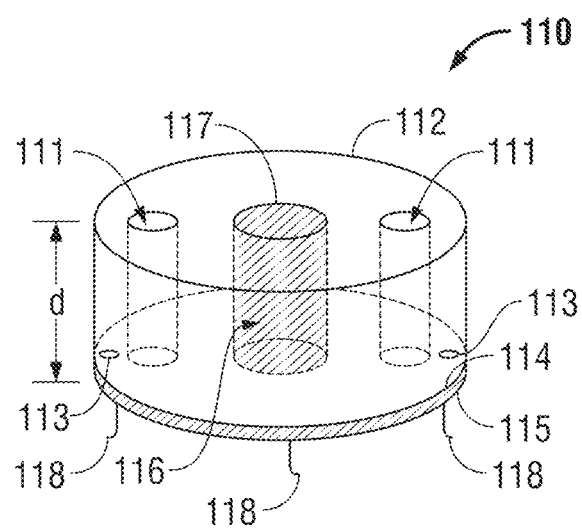
FIG. 7 is a perspective, cross-sectional view of a multi-probe dielectric spacer according to one embodiment the present disclosure.
Figure 8:
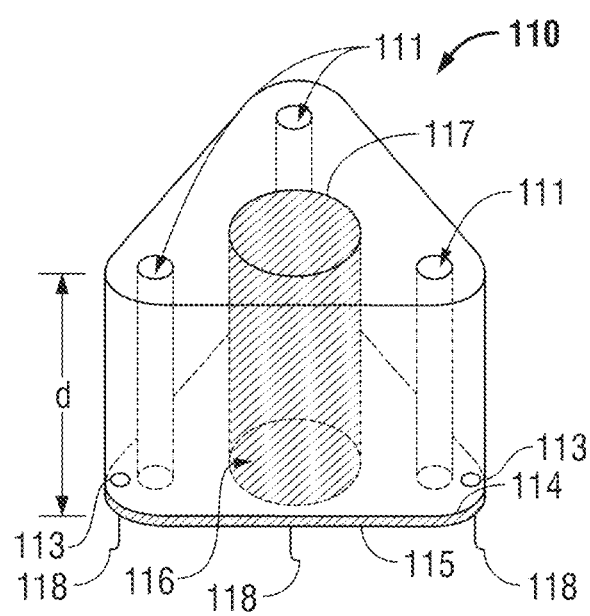
FIG. 8 is a perspective, cross-sectional view of a multi-probe dielectric spacer according to another embodiment the present disclosure.

FIG. 7 shows another embodiment of a dielectric spacer 110 having a substantially toroidal shape. The dielectric spacer 110 may also have a granular (e.g., triangular) shape as shown in FIG. 8. The spacer 110 may be formed from a solid dielectric material having a dielectric permittivity from about 2 $\varepsilon_r$ to about 80 $\varepsilon_r$. In another embodiment, the spacer 110 may include a rigid housing 112. The housing 112 has a predetermined thickness "d" that is selected based on the frequency of the microwave energy being supplied by the antenna assemblies 12. The distance "d" is selected to shift the VSWR by the predetermined amount, such that the minimum VSWR is at the surface of the tissue "T."

The housing 112 may be filled with any suitable dielectric liquid or deformable material such as water, saline, dielectric gels, and mixtures thereof. If a dielectric liquid is utilized, the housing 112 may be coupled to the coolant system 13 to provide for circulation of the coolant fluid 37 and may also include one or more temperature monitoring devices to provide for temperature-based cooling thereof as described above with respect to the spacer 90.

The spacer 110 includes two or more apertures 111 defined therethrough for insertion of the antenna assemblies 12 and into the tissue "T." In one embodiment, any number of apertures 111 may be disposed within the spacer 110 to accommodate a desired number of the antenna assemblies 12. The apertures 111 may be sized to be in frictional contact with the antenna assemblies 12 thereby preventing movement of the antenna assemblies 12 while allowing for relatively easier insertion.

The spacer 110 may also include one or more fastening elements 118 disposed on a skin-contacting bottom surface 114. The elements 118 may be hooks, barbs and other tissue-penetrating elements suitable for retaining the spacer 110. The spacer 110 may also include an adhesive layer 115 disposed on the bottom surface 114 thereof. In one embodiment, a protective film may be disposed over the adhesive layer 115 to protect the adhesive prior to use.

Figure 9:
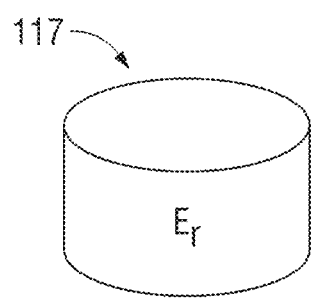
FIG. 9 is a perspective view of a dielectric insert according to one embodiment the present disclosure.

The spacer 110 also includes a centrally disposed chamber 116 having a substantially cylindrical shape and a removable dielectric insert 117 as shown in FIG. 9. The apertures 111 are disposed radially around the chamber 116. The dielectric insert 117 also has a substantially cylindrical shape suitable for insertion into the chamber 116 and may be sized to be in frictional contact with the chamber 116. In another embodiment, the chamber 116 and the dielectric insert 117 may be of any suitable symmetrical shape configured to shift the VSWR.

The dielectric insert 117 may be formed from a solid dielectric material having a dielectric permittivity from about 2 $\varepsilon_r$ to about 80 $\varepsilon_r$. The removable insert 117 configuration allows for use of various inserts 117 to provide for a suitable impedance match with the tissue "T." The insert 117 may be specifically designed for use with specific tissue types (e.g., liver, lung, kidney, bone, etc.) as well as the operational frequency of the generator 14.

Figure 10:
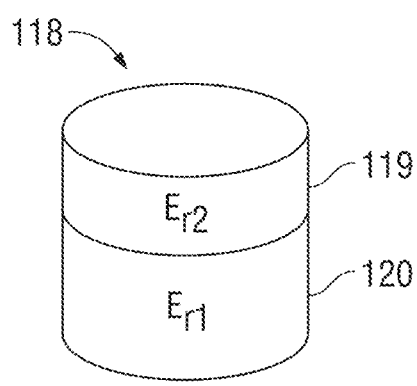
FIG. 10 is a perspective view of a dielectric insert according to another embodiment the present disclosure.

FIG. 10 shows another embodiment of a removable dielectric insert 118 having two or more stackable subassemblies 119 and 120. The first subassembly 119 is formed from a dielectric material having a first dielectric permittivity from about 2 $\varepsilon_r$ to about 80 $\varepsilon_r$. The second subassembly 120 is formed from a dielectric material having a second dielectric permittivity from about 2 $\varepsilon_r$ to about 80 $\varepsilon_r$. The first and second subassembly 119 and 120 may frictionally fit together (e.g., female and male connectors) to form the removable dielectric insert 118. The insert 118 provides additional flexibility in selecting specific material to find the ideal impedance match with the tissue "T" to shift the VSWR.

Figure 11:
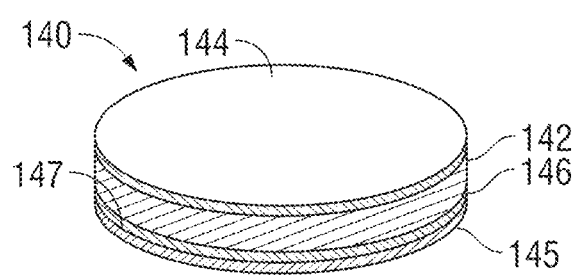
FIG. 11 is a perspective view of a dielectric spacer according to one embodiment the present disclosure.

FIG. 11 shows another embodiment of a dielectric spacer 140 having a substantially disk-like shape. The spacer 140 has a multi-layered structure and includes a gel layer 142 disposed between a top substrate 144 and a bottom substrate 146 (e.g., the top substrate 144 disposed on a top surface of the gel layer 142 and the bottom substrate 146 disposed on a bottom surface of the gel layer 142). The gel layer 142 may be formed from a dielectric, elastic, shape-memory gel, such as hydrogels or adhesives or other polymer-based materials having a dielectric permittivity from about 2 $\varepsilon_r$ to about 30 $\varepsilon_r$. The dielectric properties of the gel layer 142 shift the VSWR thereby avoiding heat damage to the surface of the tissue "T" as shown in FIG. 3.

The substrates 144 and 146 may be formed from any type of dielectric polymer-based material, such as polyurethane. The substrates 144 and 146 may be formed as a film or a foam suitable for penetration by the antennas assemblies 12. In one embodiment, the substrates 144 and 146 may be formed from thermal paper for indicating changes in the temperature of the tissue "T." The spacer 140 may also include an adhesive layer 145 disposed on a skin-contact bottom surface 147 of the bottom substrate 146. In one embodiment, a protective film may be disposed over the adhesive layer 145 to protect the adhesive prior to use.

In one embodiment, the substrates 144 and 146 and the gel layer 142 may have one or more openings (not explicitly shown) defined therein to facilitate insertion of the antenna assemblies 12. In another embodiment, the substrates 144 and 146 and the gel layer 142 may be contiguous such that the antenna assemblies 12 perforate the multiple layers during insertion. The gel and/or adhesives of the gel layer 142 maintains the antenna assemblies 12 at the desired depth thereby preventing displacement thereof during ablation.

Figure 12A:
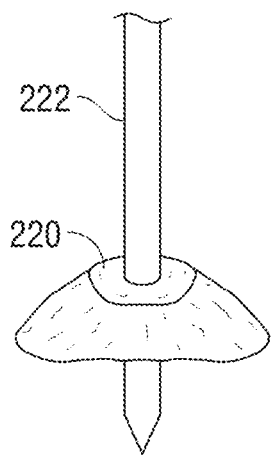
FIG. 12A is a perspective view of a dielectric spacer apparatus according to an embodiment of the present disclosure.
Figure 12B:
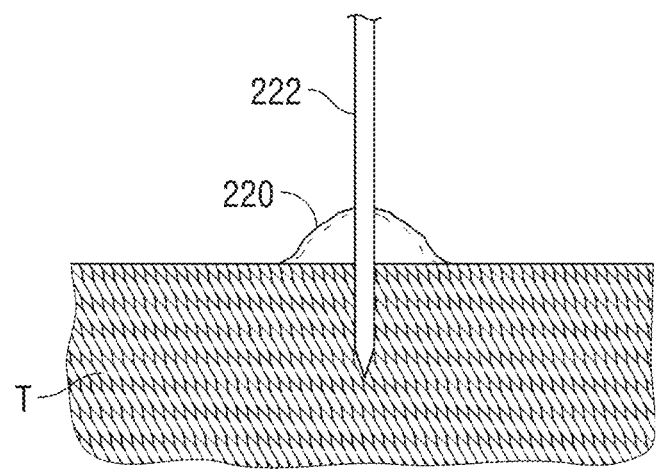
FIG. 12B is a side, cross-sectional view of the dielectric spacer of FIG. 12A.

FIGS. 12A-12B show a dielectric spacer 220 for shifting the VSWR of an antenna assembly 222 within the tissue "T" (FIG. 12A). The dielectric spacer 220 may be formed from a dielectric, elastic, shape-memory gel, such as hydrogels or adhesives or other polymer-based materials having a dielectric permittivity from about 2 $\varepsilon_r$ to about 80 $\varepsilon_r$. In one embodiment, the dielectric spacer 220 may be formed from various particles (e.g., polymer, ceramic, etc.) mixed with the hydrogels or adhesives. The dielectric spacer 220 may be utilized as a formed (e.g., gel layer 142) or unformed gel layer (as shown) for insertion of the antenna assembly 222 therethrough.

In one embodiment, the dielectric spacer 220 may be formed from an adhesive amorphous putty that may be molded under pressure but is still capable of retaining its shape. In other words, the putty may be shaped from a first configuration into a subsequent configuration for securing the antenna assembly 222 therein. In one embodiment, the amorphous putty may be a viscoelastic polymer composition having a siloxane polymer, a crystalline material and one or more thixotropic agents to reduce liquid properties thereof and enable the amorphous putty to hold its shape.

During use, the dielectric spacer 220 is placed onto the tissue "T" and the antenna assembly 222 is inserted therethrough perforating the dielectric spacer 200. The viscoelastic properties of the spacer 220 allow the antenna assembly 222 to easily penetrate therethrough and into the tissue "T" as shown in FIG. 12B. Since the putty of the spacer 220 is adhesive, the putty secures the spacer 220 to the tissue "T" and maintains the position of the antenna assembly 222 therein. The above-discussed embodiments of dielectric spacers may also be utilized with a spreadable dielectric gel layer (e.g., ultrasound gel, petroleum gel, etc.) to provide for additional VSWR shifting.

The described embodiments of the present disclosure are intended to be illustrative rather than restrictive, and are not intended to represent every embodiment of the present disclosure. Various modifications and variations can be made without departing from the spirit or scope of the disclosure as set forth in the following claims both literally and in equivalents recognized in law.

What is claimed is:

1. A system for use during microwave ablation of tissue, the system comprising:
   a microwave antenna configured to deliver microwave energy to a patient;
   a dielectric spacer including:
      a conformable housing including:
         an outer surface extending between a first end surface and an opposite, second end surface;
         an inner surface extending between the first and second end surfaces, the inner surface defining a lumen extending through the first and second end surfaces and that receives the microwave antenna therethrough; and
         an interior surface bounded by the outer surface, first end surface, and second end surface, the interior surface defining a cavity including a dielectric material that expands the housing to a thickness that is determined based on a frequency of the microwave energy delivered to the patient by the microwave antenna received through the lumen;
   a cooling system in fluid communication with the cavity and configured to circulate the dielectric material through the cavity; and
   a skin temperature monitoring sensor disposed on the outer surface of the conformable housing and operably coupled to the cooling system, the skin temperature monitoring sensor monitoring a surface temperature of the patient's skin to which the housing is conformed, wherein the cooling system controls at least one of a flow of the dielectric material to the cavity or a temperature of the dielectric material based on the monitored surface temperature of the patient's skin during delivery of the microwave energy to the patient by the microwave antenna.

2. The system according to claim 1, wherein the dielectric material is a coolant.

3. The system according to claim 2, wherein the coolant is selected from the group consisting of water and saline.

4. The system according to claim 1, wherein the thickness of the housing minimizes a voltage standing wave ratio at the patient's skin to which the housing is conformed.

5. A system for use during microwave ablation of tissue, the system comprising:
   a microwave antenna configured to deliver microwave energy to a target within a patient's body;
   a dielectric spacer having a flexible housing for placement on the patient's skin, the flexible housing defining a cavity surrounding a lumen extending through opposing sides of the flexible housing, the microwave antenna insertable through the lumen for placement at the target within the patient's body;
   a cooling system in fluid communication with the cavity defined by the flexible housing for delivering a cooling fluid to the cavity to expand the flexible housing to a thickness that is determined based on a frequency of the microwave energy delivered to the target within the patient's body by the microwave antenna while received through the lumen; and a skin temperature monitoring sensor disposed on an outer surface of the flexible housing for monitoring an outer surface temperature of the patient's skin on which the flexible housing is placed, wherein the cooling system controls at least one of a flow of the cooling fluid to the cavity or a temperature of the dielectric material based on the monitored outer surface temperature of the patient's skin during delivery of the microwave energy to the target within the patient's body.

6. The system according to claim 5, wherein the thickness of the flexible housing minimizes a voltage standing wave ratio at the patient's skin on which the flexible housing is placed.

\* \* \* \* \*